United States Patent [19]
Astle

[11] Patent Number: 5,958,343
[45] Date of Patent: Sep. 28, 1999

[54] SMALL VOLUME PIPETTOR

[76] Inventor: Thomas W. Astle, 607 Harborview Rd., Orange, Conn. 06477

[21] Appl. No.: 08/998,847

[22] Filed: Dec. 29, 1997

[51] Int. Cl.$^6$ ...................................................... G01N 1/14
[52] U.S. Cl. ............................ 422/100; 422/63; 422/81; 422/103; 436/54; 436/180; 73/864.01; 73/864.16; 73/864.17
[58] Field of Search ............... 422/63, 67, 68.1, 422/81, 100, 103; 436/52, 180, 54; 73/863.1, 863.73, 864.01, 864.16, 864.17

[56] References Cited

U.S. PATENT DOCUMENTS

| | | | |
|---|---|---|---|
| 4,615,468 | 10/1986 | Gay | 222/327 |
| 5,104,625 | 4/1992 | Kenney | 422/100 |
| 5,236,666 | 8/1993 | Hulette et al. | 422/65 |
| 5,648,266 | 7/1997 | Astle | 435/308.1 |
| 5,660,796 | 8/1997 | Sheehy | 422/100 |
| 5,730,938 | 3/1998 | Carbonari et al. | 422/64 |
| 5,770,160 | 6/1998 | Smith et al. | 422/100 |
| 5,776,418 | 7/1998 | Besnier et al. | 422/68.1 |

*Primary Examiner*—Long V. Le
*Attorney, Agent, or Firm*—John H. Crozier

[57] ABSTRACT

In a preferred embodiment, a small volume pipettor, including: a plurality of pistons; a plurality of liquid delivery needles; motive device to cause one of the pistons to move axially within one of the needles to cause a liquid to be selectively drawn into and discharged from the needle; sealing apparatus disposed around the pistons to effect sealing of upper ends of the needles; assembly apparatus in which the needles and the sealing apparatus are disposed; and apparatus to permit the assembly apparatus to be removed from the pipettor as a one-piece unit. Further provided are novel apparatus to seal upper ends of the needles around the pistons.

8 Claims, 4 Drawing Sheets

5,958,343

SMALL VOLUME PIPETTOR

BACKGROUND OF THE INVENTION

1. Field of the Invention

The present invention relates to pipettors generally and, more particularly, but not by way of limitation, to a novel pipettor especially useful in transferring small volumes of liquid.

2. Background Art

In the field of biotechnology, there has been a constant effort to increase the quantity of bioassay-type experiments. This is particularly true in the specific areas of "high throughput screening" for new drugs and human genome research. As the volume of tests increases, so does the corollary of costs. Tests that were originally done in 16 mm test tubes, moved to 96 tests at a time in the microplate format (8×12 wells on 9 mm centers). Now, there is increased interest in further miniaturization in a 384-well format. In the same size as the microplate (3.3"×5"), there are 384 wells in a 16 by 24 array on 4.5 mm centers. The individual well volume decreases from approximately 300 microliters per well in the microplate down to less than 100 microliters per well. The resulting benefit is reduced usage of the costly reagents used in testing.

The tight spacing of a 384-well plate, 4.5 mm center-to-center plate, essentially eliminates the possibility of manual pipetting, due to the very tedious effort involved. The conventional automated X-Y-Z bridge pipettors can be used, but they are limited to from 1 to 8 needles at a time, again due to the physical limitation of 4.5 mm center-to-center spacing. Thus there is clearly a need for a faster method of transferring liquid samples to and from such wells.

There are three basic considerations which must be addressed. First, since small volumes (i.e., less than 100 microliters) are to be pipetted, accuracy and precision of delivery is required. Second, in most applications, carryover between samples must be eliminated, or at the least, minimized. Third, the tight spacing between wells presents sealing problems and force problems that do not exist on the larger scale of 9 mm center-to-center spacing such as used in microplates.

Accordingly, it is a principal object of the present invention to provide a small volume pipettor which provides accuracy and precision of delivery of liquid samples.

It is a further object of the invention to provide such a small volume pipettor in which carryover between samples is minimized or eliminated.

It is an additional object of the invention to provide such a small volume pipettor which overcomes the sealing problems and force problems inherent in simultaneously pipetting a large number of liquid samples.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a small volume pipettor, comprising: a plurality of pistons; a plurality of liquid delivery needles; motive means to cause one of said pistons to move axially within one of said needles to cause a liquid to be selectively drawn into and discharged from said needle; sealing means disposed around said pistons to effect sealing of upper ends of said needles; assembly means in which said needles and said sealing means are disposed; and means to permit said assembly means to be removed from said pipettor as a one-piece unit. Further provided are novel means to seal upper ends of said needles around said pistons.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1:
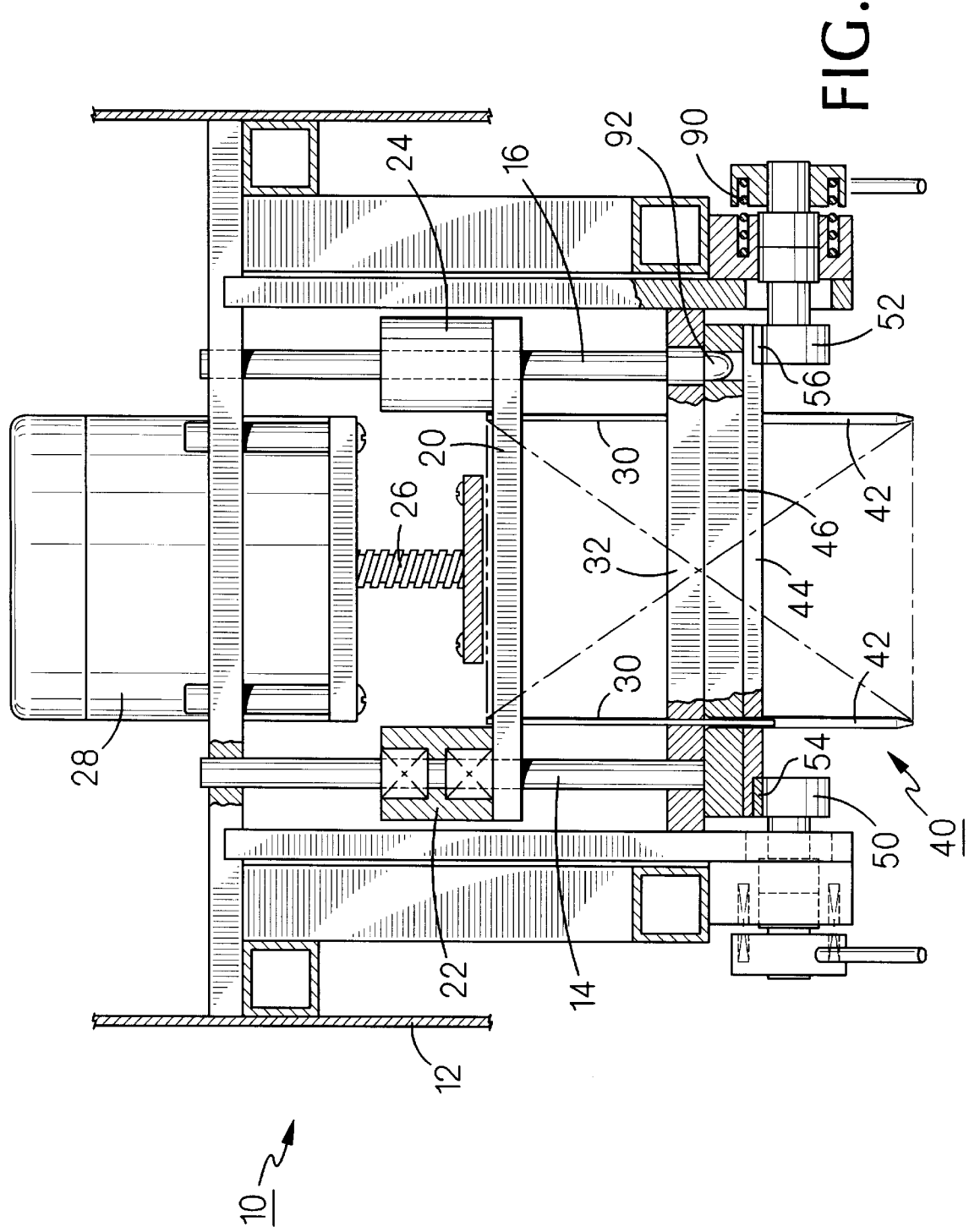
FIG. 1 is a side elevational view, partially in cross-section and partially cut-away, of a pipettor constructed according to the present invention.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

FIG. 1 illustrates a pipettor, constructed according to the present invention, and generally indicated by the reference numeral 10.

Pipettor 10 includes a frame/housing 12 in which are fixedly mounted two vertical guide rods 14 and 16. A piston drive plate 20 has two linear ball bushings 22 and 24 fixedly disposed at either side thereof through which vertical guide rods 14 and 16 extend, respectively. Piston drive plate 20 is selectively raised or lowered along guide rods 14 and 16 by means of threaded lead screw 26 driven by a stepper motor linear actuator 28. A plurality of pistons, as at 30, are fixedly attached at their upper ends through piston drive plate 20. It may be assumed that the total number of pistons 30 is a relatively large number, say for example, 384. The lower ends of pistons 30 extend through corresponding holes defined through a lower head plate 32 to which plate are fixedly attached the lower ends of vertical guide rods 14 and 16.

A tip assembly, generally indicated by the reference numeral 40, includes a plurality of needles, as at 42, which are carried in a horizontal lower needle mounting plate 44 adjacent a horizontal upper needle mounting plate 46. The number of needles 42 will typically be equal to the number of pistons 30, although the number of needles may differ from the number of pistons if not all pistons and/or needles are to be used in a particular application. As shown on FIG. 1, pistons 30 and needles 42 are arranged such that each piston is axially inserted in a needle and is vertically moveable therein by the operation of motor 28. Because of the scale of FIG. 1, the details of the sealing arrangement for pistons 30 and needles 42 are not shown.

Tip assembly 40 is held to lower head plate 32 by means of two eccentric cams 50 and 52 which releasably mate, respectively, to wear plates 54 and 56. Applying rotational force to cams 50 and 52 rotates the cams locks tip assembly 40 in place.

Prior to removing tip assembly 40, motor 28 withdraws pistons 30 from needles 42 and lower needle mounting plate 44 and upper needle mounting plate 46, so that the pistons are completely withdrawn from the elements of tip assembly 40. Then, relieving eccentric clamp pressure allows spring 90 to move cam 52 outwardly to clear lower needle mounting plate 44. Cam 50 is similarly moved outwardly. Tip assembly 40 can now be removed for cleaning or replacement with a already clean tip assembly.

To install tip assembly 40, pistons 30 must remain in their elevated and clear position. Tip assembly 40 is then located in place by guide pins 92 disposed at the lower ends of guide rods 14 and 16 (only the guide pin on guide rod 16 is shown on FIG. 1). With tip assembly 14 in place, cams 50 and 52 are pushed in and rotated to effect locking.

Each piston 30 must be sealed to the corresponding needle 42. Since a large number of seals is required, each seal must have very low frictional drag forces, but still must effectively seal the moving piston surface.

Figure 2:
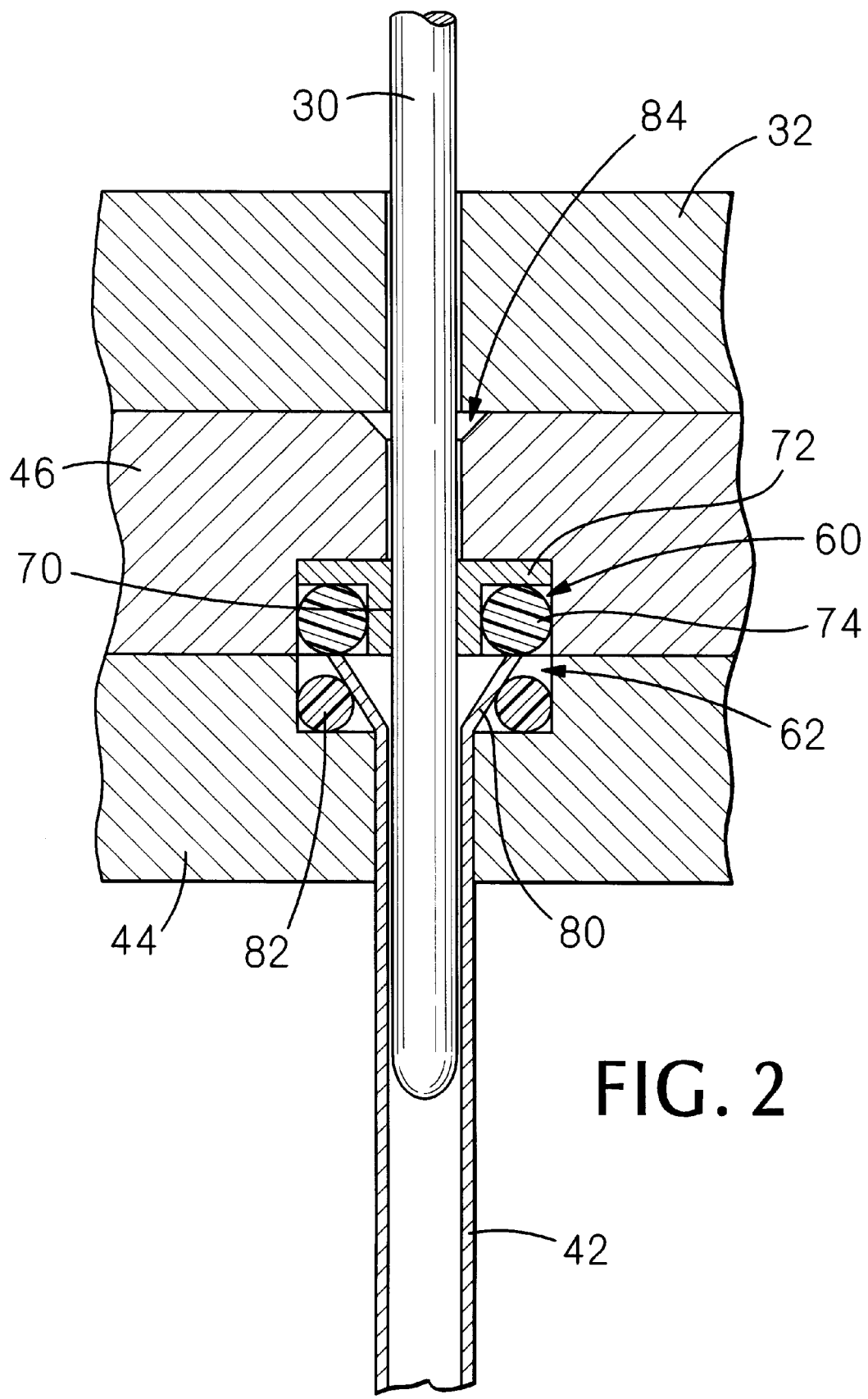
FIG. 2 is a fragmentary side elevational view, partially in cross-section, of one method of sealing a piston to its displacement cylinder.

FIG. 2 illustrates one sealing method for sealing a piston 30 and a needle 42. First and second aligned bores 60 and 62 are defined, respectively, in the lower surface of upper needle mounting plate 46 and in the upper surface of lower needle mounting plate 44. Disposed in bore 60 and closely fitting around the outer periphery of piston 30 is a vertical cylindrical seal 70, with an outwardly extending flange 72 formed at the upper end of the seal. A first O-ring 74 encircles the outer periphery of seal 70 to serve as a tensioning garter spring to provide clamping force between the cylindrical seal 70 and piston 30 so as to maintain a tight seal therebetween.

The top of needle 42 terminates in a V-shaped form 80 disposed in bore 62. A second O-ring 82 is disposed around the outer periphery of form 80 provides additional sealing. Thus arranged, the vertical alignment of needle 42 is fixed by first and second O-rings 74 and 82, with the edge of form 80 bearing against the lower edge of the first O-ring, providing downward force on the needle, while the second O-ring provides upward force on the needle. The amount of "squeezing" of O-rings 74 and 82 can be increased by selectively milling a small amount from the upper surface of lower needle mounting plate 44 and/or the lower surface of upper needle mounting plate 46.

An upwardly open V-shaped opening 84 is defined in the upper surface of upper needle mounting plate 46, axially disposed with respect to the other elements described above on Figure to to serve as a lead-in for piston 30 to guide the piston to the center of seal 70, thereby eliminating damage to the seal. The lower end of piston 30 is rounded to further eliminate any possible seal damage. As motor 28 (FIG. 1) lowers piston 30 into seal 70, the piston and the seal close off the upper end of the needle at the seal.

The material of seal 70 may be selected from available fluoropolymers depending on the specific application. This design takes advantage of the cold flow properties of fluoropolymers to maintain a uniform seal over an extended period of time. First and second O-rings 74 and 82 may be formed from any suitable elastomeric material. With the other elements of tip assembly 40 constructed of chemically resistant materials, such as stainless steel, with or without a fluoropolymer type coating, chemical means may be employed for cleaning the tip assembly between uses. A 10–20% solution of household bleach is commonly used. However, in some applications, a more rigorous cleaning and sterilizing function, such as autoclaving, is required.

Figure 3:
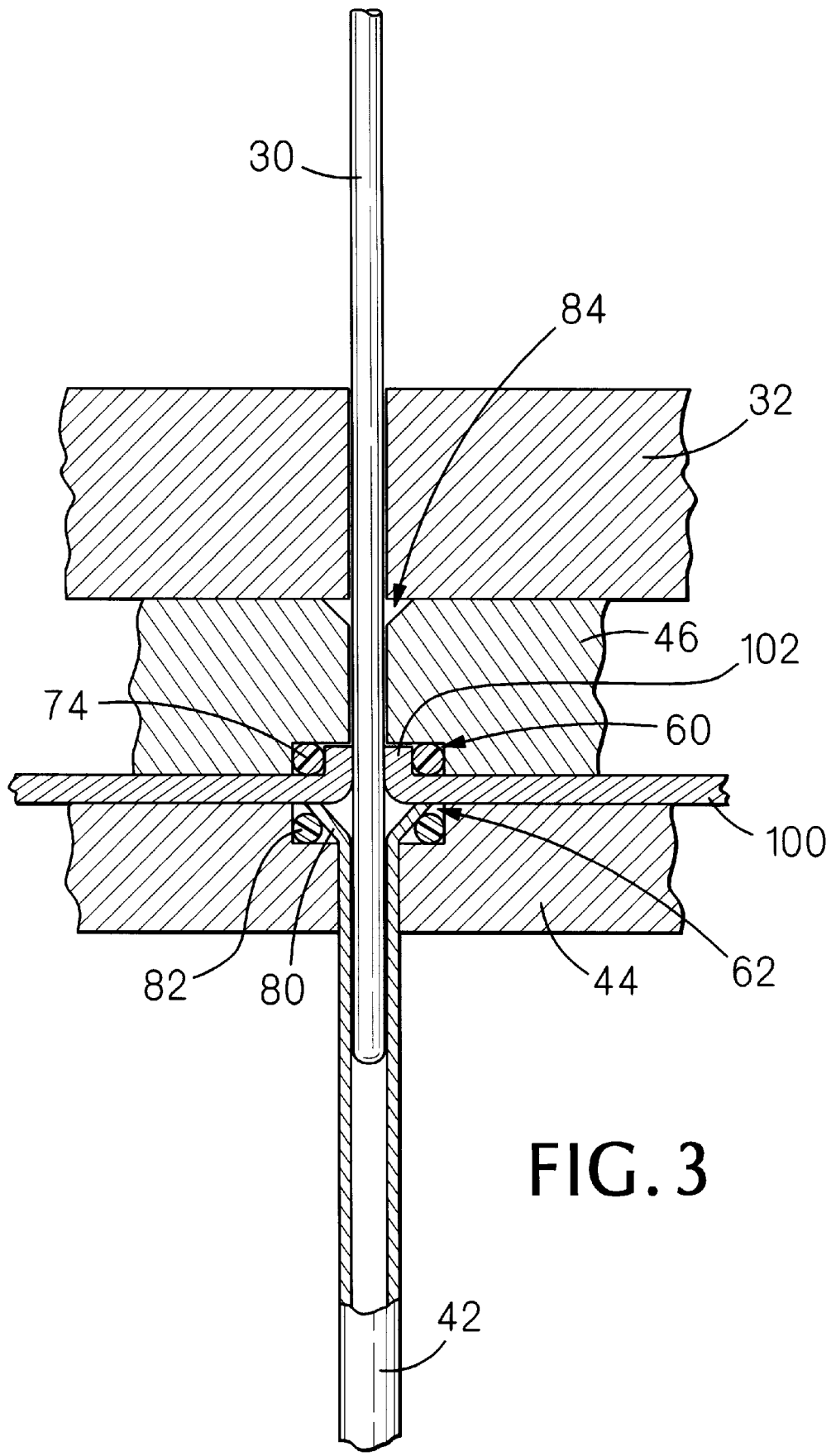
FIG. 3 is a fragmentary side elevational view, partially in cross-section, of another method of sealing a piston to its displacement cylinder.

Another method of sealing is illustrated on FIG. 3 where elements having the same form and function of like elements are on FIG. 2 are given the same reference numerals as on FIG. 2. Here, individual seal 70 (FIG. 2) have been replaced with a molded sheet 100 of fluoropolymer material disposed between upper and lower needle mounting plates 46 and 44. Piston 30 is surrounded by a section 102 of sheet 100, with the diameter of the opening of section 102 being slightly less than the diameter of the piston and having an upwardly open frusto-conical shape when the piston is not inserted therethrough. It will be understood that similar seals will be provided by sheet 100 for other pistons in pipettor 10 (FIG. 1).

The choice between the different sealing methods shown on FIGS. 2 and 3 is one of manufacturing suitability, one common sheet or seal 100 (FIG. 3) being easier to handle than a large number of tiny individual seals (FIG. 2).

Figure 4:
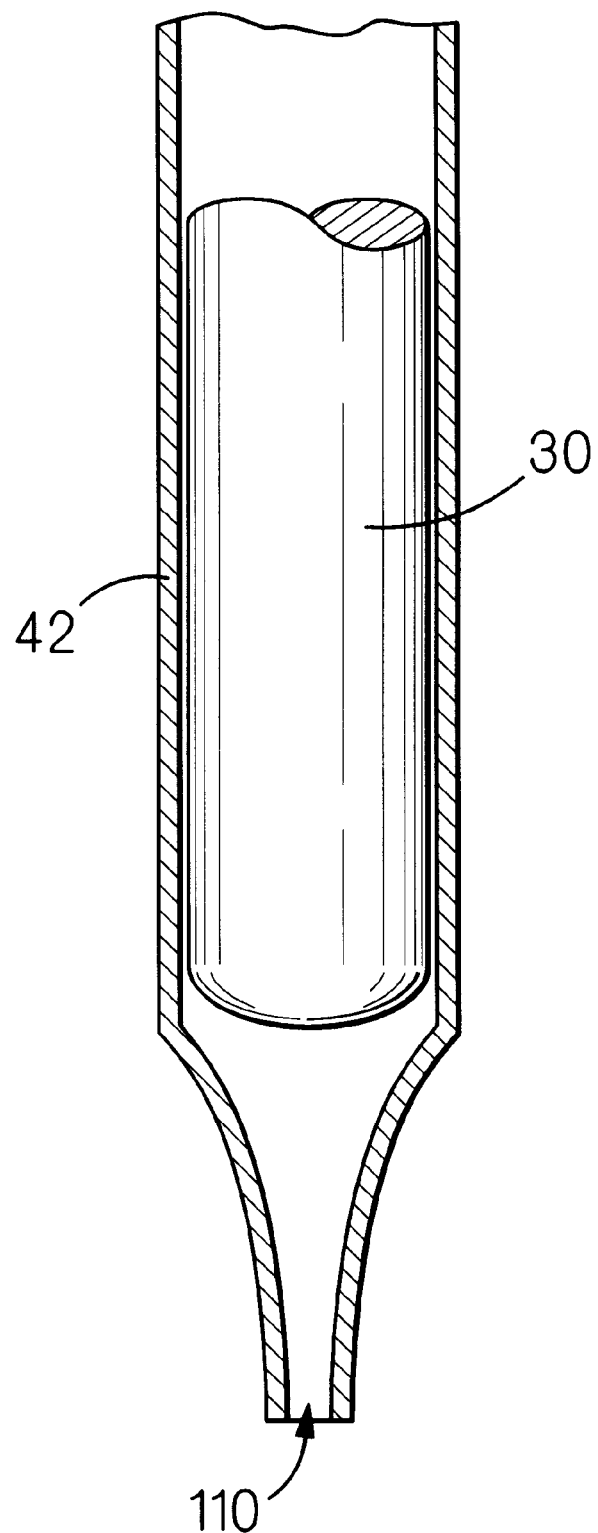
FIG. 4 is a fragmentary side elevational view, partially in cross-section, of the tip of a delivery needle constructed according to the present invention.

FIG. 4 illustrates piston 30 at its lowest position in needle 42, in which position the piston has forced substantially all the contents of the bore of the needle out of a needle exit orifice 110. To provide the accuracy and precision required, the present invention utilizes a positive displacement approach. Piston 30, within the enclosed cylindrical space of needle 42 is designed to move nearly to exit orifice 110. Thus, the only displacement air is the fit between the inside diameter of needle 42 and the diameter of piston 30, which displacement can be held very small.

The maximum volume needle 42 can deliver is a function of its length and inside diameter. These both have practical limits. The diameter of orifice 110 is another important parameter. It is desirable to deliver very small volumes, of 0.5 microliter or less. To do this, exit orifice 110 must be very small to minimize the effect of surface tension. Ideally, it is desirable to have the exit velocity from needle 42 high enough to overcome the surface tension forces and deliver as a stream. This is difficult to achieve within the economic limits commonly applied to these types of pipettors. Therefore, by keeping the orifice diameter as small as feasible, the drop size on delivery is minimized and, concomitantly, the velocity of the liquid exiting needle 42 is maximized.

It has been found that, with the use of a #17 gauge thin wall hypodermic needle and swaging the tip of the needle as shown on FIG. 4, using conventional techniques, the drop size is economically minimized and the velocity of the exiting liquid is maximized. Total delivery volume is approximately 60 microliters with a 2.5-inch piston stroke. The tips are swaged over a mandrel, producing a tip with an inwardly curving wall converging toward exit orifice 110. Typical dimensions with such an arrangement, in inches, are as follows:

ID of piston: 0.045
ID of needle: 0.047
OD of needle: 0.058
ID of orifice: 0.015

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A volume pipettor apparatus, comprising:

(a) a plurality of pistons;

(b) a plurality of liquid delivery needles;

(c) motive means to cause one of said plurality of pistons to move axially within one of said plurality of needles to cause a liquid to be selectively drawn into and discharged from said one of said plurality of needles;

(d) sealing means disposed around said pistons to effect sealing of upper ends of said needles;

(e) assembly means in which said needles and said sealing means are disposed;

(f) means to permit said assembly means to be removed from said pipettor apparatus as a one-piece unit;

(g) a generally cylindrical seal surrounding and in contact with said one of said pistons; and (h) a first O-ring encircling said generally cylindrical seal to serve as a tensioning garter spring to effect a tight seal between said generally cylindrical seal and said one of said pistons.

2. A volume pipettor apparatus, as defined in claim 1, further comprising: an upper end of said one of said plurality of needles terminating in a V-shaped form, with an upper rim of said V-shaped form engaging a lower surface of said first O-ring, with said first O-ring providing a downward force on said one of said plurality of needles.

3. A volume pipettor apparatus, as defined in claim 2, further comprising: a second O-ring encircling said V-shaped form, with said second O-ring providing an upward force on said one of said plurality of needles.

4. A volume pipettor apparatus, as defined in claim 3, wherein:

(a) said assembly means includes adjacent upper and lower needle mounting plates having defined therein, respectively, first and second aligned bores;

(b) said first bore has substantially disposed therein said seal and said first O-ring; and (c) said second bore has substantially disposed therein said V-shaped form and said second O-ring.

5. A volume pipettor apparatus, as defined in claim 1, wherein: said generally cylindrical seal includes an outwardly extending flange formed at an upper end of said generally cylindrical seal and disposed above said first O-ring.

6. A volume pipettor apparatus, as defined in claim 1, wherein:

(a) said assembly means includes upper and lower needle mounting plates; and (b) said generally cylindrical seal is formed in a sheet extending between said upper and lower needle mounting plates.

7. A volume pipettor apparatus, as defined in claim 6, wherein: said generally cylindrical seal has a diameter less than that of said one of said plurality of pistons and has a frusto-conical shape when said one of said plurality of pistons is not inserted through said generally cylindrical seal.

8. A volume pipettor apparatus, as defined in claim 1, wherein: said means to permit permits said assembly means to be removed from said pipettor apparatus when said pistons have been fully withdrawn from said assembly means.

* * * * *